(12) United States Patent
Endo et al.

(10) Patent No.: US 9,101,300 B2
(45) Date of Patent: Aug. 11, 2015

(54) INTRAOCULAR LENS POWER DETERMINATION APPARATUS, INTRAOCULAR LENS POWER DETERMINATION METHOD, AND INTRAOCULAR LENS POWER DETERMINATION PROGRAM

(71) Applicant: NIDEK CO., LTD., Gamagori-shi, Aichi (JP)

(72) Inventors: Masakazu Endo, Okazaki (JP); Masaaki Hanebuchi, Nukata-gun (JP)

(73) Assignee: NIDEK CO., LTD., Gamagori (JP)

( * ) Notice: Subject to any disclaimer, the term of this patent is extended or adjusted under 35 U.S.C. 154(b) by 195 days.

(21) Appl. No.: 13/664,751

(22) Filed: Oct. 31, 2012

(65) Prior Publication Data

US 2013/0107208 A1 May 2, 2013

(30) Foreign Application Priority Data

Oct. 31, 2011 (JP) ................................. 2011-239736

(51) Int. Cl.
*A61B 3/14* (2006.01)
*A61B 3/10* (2006.01)

(52) U.S. Cl.
CPC .... *A61B 3/14* (2013.01); *A61B 3/10* (2013.01)

(58) Field of Classification Search
CPC ........ A61B 3/14; A61B 3/102; A61B 3/0025; A61B 3/113; A61B 3/12; A61B 3/0008; A61B 3/107; A61B 3/1005; A61B 3/1015; A61B 3/1025; A61B 3/10; A61B 3/103; A61B 3/117; A61B 3/145; A61B 3/0058; A61B 3/112; A61B 3/13; A61B 3/18

USPC ......... 351/200, 205, 206, 207, 208, 209, 210; 396/18

See application file for complete search history.

(56) References Cited

U.S. PATENT DOCUMENTS 5,968,095 A 10/1999 Norrby
2008/0231809 A1* 9/2008 Haigis ........................... 351/246

(Continued)

FOREIGN PATENT DOCUMENTS

JP A-2007-505716 3/2007
WO WO 2008/148517 A1 12/2008
WO WO 2010/109020 A1 * 9/2010

OTHER PUBLICATIONS

Nov. 25, 2014 Office Action issued in European Application No. 12190313.2.

(Continued)

*Primary Examiner* — William Choi
*Assistant Examiner* — Sharrief Broome
(74) *Attorney, Agent, or Firm* — Oliff PLC

(57) ABSTRACT

An intraocular lens power determination apparatus for determining a highly precise IOL power, the apparatus including: an anterior segment imaging device for obtaining a cross-sectional image of an anterior segment by detecting reflection from the anterior segment of an examinee's eye; and a power calculation unit obtaining an offset distance from a front surface of a lens to a point of contact of a Zinn's zonule with the lens based on the anterior segment cross-sectional image obtained by the anterior segment imaging device and calculating a prospective postoperative anterior chamber depth by adding the offset distance to an anterior chamber depth of an eye so that the IOL power is calculated by using the prospective postoperative anterior chamber depth.

20 Claims, 3 Drawing Sheets

(56) References Cited

U.S. PATENT DOCUMENTS

2009/0254071 A1 10/2009 Williamson et al.
2010/0191230 A1 7/2010 Dick et al.
2011/0052020 A1 3/2011 Hildebrand et al.

OTHER PUBLICATIONS

Mar. 6, 2013 Extended European Search Report issued in European Application No. 12190313.2.

* cited by examiner

INTRAOCULAR LENS POWER DETERMINATION APPARATUS, INTRAOCULAR LENS POWER DETERMINATION METHOD, AND INTRAOCULAR LENS POWER DETERMINATION PROGRAM

This application is based upon and claims the benefit of priority from the prior Japanese Patent application No. 2011-239736, filed Oct. 31, 2011, the entire contents of which are incorporated herein by reference.

BACKGROUND OF THE INVENTION

1. Field of the Invention

The present invention relates to an apparatus, a method, and a program for determining a power of an intraocular lens which is injected into an eye in a cataract surgery.

2. Related Art

In a cataract surgery, in order to determine (calculate) a power (diopter) of an intraocular lens (hereinafter, referred to as an IOL) to be injected into an examinee's eye after a nucleus lentis is removed from the eye, the examinee's eye is measured to obtain its specified characteristics data such as corneal refractive power and an ocular axial length. Based on these data, the power of the IOL is calculated according to an IOL calculation formula created by experiences or theories. As the IOL calculation formula, an SRK formula, an SRK/T formula, and others are known (see Patent Document 1).

For each IOL calculation formula, a preset lens constant (for example, A-constant) is used. The lens constant is determined as a design matter according to each IOL model (model number) by an IOL manufacturer.

RELATED ART DOCUMENTS

Patent Documents

Patent Document 1: JP2007-505716A

SUMMARY OF INVENTION

Problems to be Solved by the Invention

However, a part of the IOL calculation formula to obtain a prospective anterior chamber depth is based on clinical data, and therefore the IOL power to be calculated could be less accurate regarding an eye that has a nonstandard eyeball shape.

Taking the SRK/T formula as an example, a value of a prospective postoperative anterior chamber depth is obtained by the calculation formula introduced by numerous clinical data. When the prospective postoperative anterior chamber depth is calculated by the SRK/T formula, the calculation is conducted with an A-constant, a corneal curvature radius, and an ocular axial length. Specifically, the prospective postoperative anterior chamber depth is obtained by an addition of a theoretical factor based on an eyeball shape and an empirical factor based on the clinical data. However, the above conventional way of calculation has a problem that an error regarding the prospective postoperative anterior chamber depth could be large, leading to an error of the IOL power.

The present invention has been made to solve the above problem and has a purpose to provide an apparatus and a program capable of determining a highly accurate IOL power.

Means of Solving the Problems

To solve the above problem, the present invention has the following configuration.

(1) First aspect of the present invention is an IOL power determination method including the steps of: obtaining a cross-sectional image of an anterior segment of an examinee's eye by detecting reflection from the anterior segment using an anterior segment imaging device; obtaining an offset distance from a front surface of a lens to a point of contact of a Zinn's zonule with the lens based on the anterior segment cross-sectional image; and calculating a prospective postoperative anterior chamber depth by adding the offset distance to an anterior chamber depth of an eye, wherein an intraocular lens power is calculated by using the prospective postoperative anterior chamber depth.

(2) Second aspect of the present invention is an IOL power determination apparatus comprising: an anterior segment imaging device arranged to obtain a cross-sectional image of an anterior segment by detecting reflection from the anterior segment of an examinee's eye; and a power calculation unit arranged to obtain an offset distance from a front surface of a lens to a point of contact of a Zinn's zonule with the lens based on the anterior segment cross-sectional image obtained by the anterior segment imaging device, calculate a prospective postoperative anterior chamber depth by adding the offset distance to an anterior chamber depth of an eye, and conduct an intraocular lens power calculation using the prospective postoperative anterior chamber depth.

(3) Third aspect of the present invention is an IOL power determination program recorded on a non-transitory computer readable medium product for instructing a computer to execute: a first step of obtaining an offset distance from a front surface of a lens to a point of contact of a Zinn's zonule with the lens based on a cross-sectional image of an anterior segment obtained by an anterior segment imaging device; a second step of calculating a prospective postoperative anterior chamber depth by adding the offset distance obtained in the first step to an anterior chamber depth of an eye; and a third step of conducting an intraocular lens power calculation using the prospective postoperative anterior chamber depth calculated in the second step.

Effects of the Invention

According to the present invention, a highly accurate IOL power can be determined.

DESCRIPTION OF EMBODIMENTS

Figure 1:
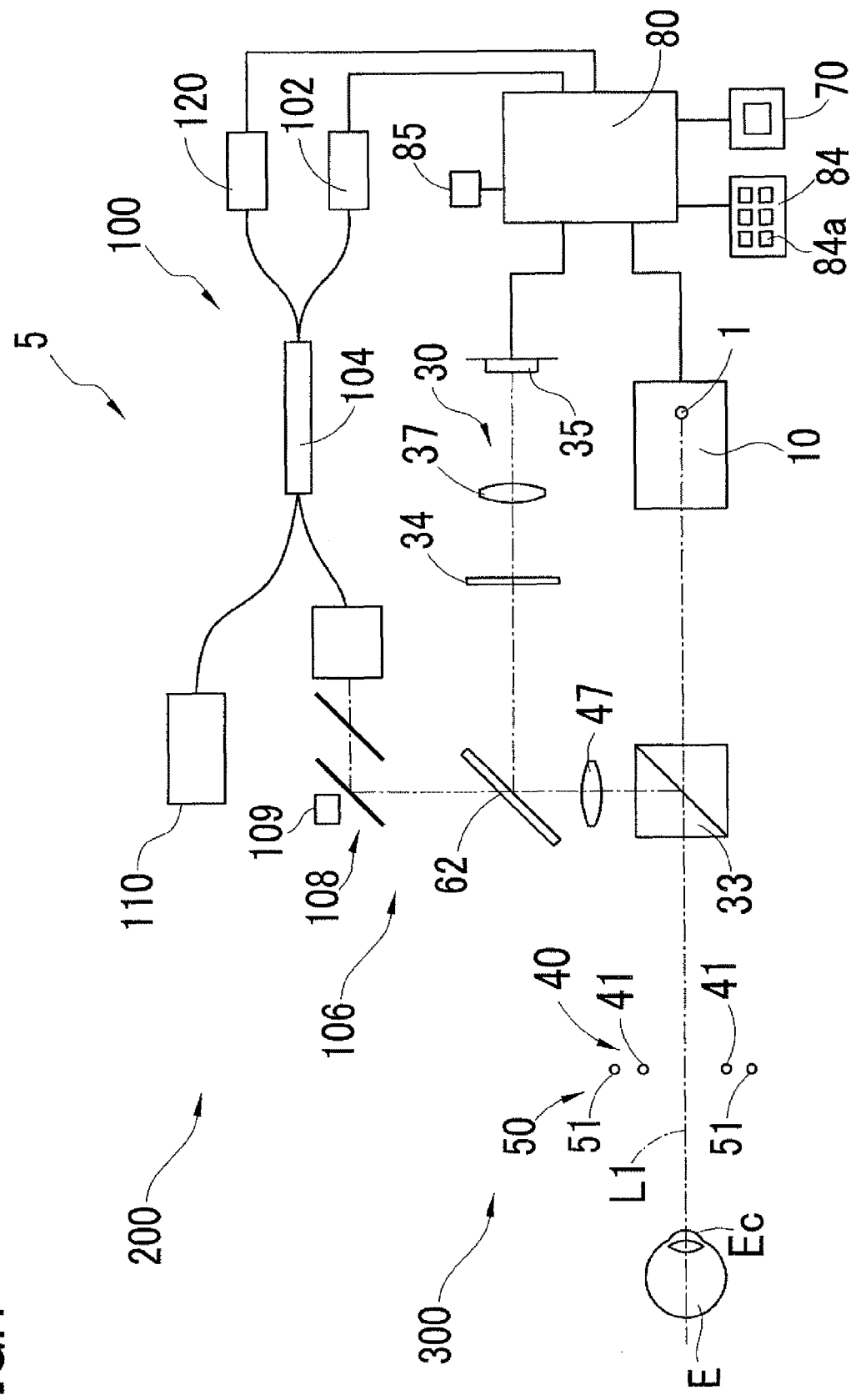
FIG. 1 is a schematic diagram explaining a configuration of an IOL power determination apparatus according to a present embodiment.

As follows, a detailed embodiment according to the present invention is explained with reference to the accompanying drawings. FIG. 1 is a schematic diagram showing a configuration of an optical system of an IOL power determination system 200 according to the present embodiment. The following optical system is accommodated in a not-shown housing. The housing is three-dimensionally moved with respect to an examinee's eye E via an operation member (for example, a joy stick) by driving a known alignment moving mechanism. In the following explanation of the present embodiment, an axial direction of the examinee's eye (eye E) is referred to as a Z direction, a horizontal direction as an X direction, and a vertical direction as a Y direction. A front surface of a fundus may be regarded as an X-Y direction.

The following explanation is made with exemplifying the IOL power determination system 200 constituted with an optical coherence tomography device (OCT device) 5, an axial length measuring device 10, and a corneal shape measuring device 300.

The OCT device 5 is used as an anterior segment imaging device for photographing a cross-sectional image of the examinee's eye E. The axial length measuring device 10 is used for measuring an axial length of the eye E. The corneal shape measuring device 300 is used for measuring a corneal shape. Herein, the OCT device 5 is explained with exemplifying an optical coherence tomography device for photographing a tomographic image (cross-sectional image) of an anterior segment.

The OCT device 5 includes an interference optical system (OCT optical system) 100. The OCT optical system 100 irradiates the eye E with measurement light. The OCT optical system 100 detects an interference state of the measurement light reflected on an anterior segment (for example, a lens) and reference light by use of an light receiving element (detector 120). The OCT optical system 100 includes an irradiation point changing unit (for example, an optical scanner 108) changing an irradiation point of the measurement light on the anterior segment in order to change an imaging position on the anterior segment. A controller 80 controls an operation of the irradiation point changing unit based on the defined imaging positional information to obtain a tomographic image based on a light receiving signal from the detector 120.

The OCT optical system 100 has a device configuration as a so-called ophthalmic optical coherence tomography (OCT). The OCT optical system 100 splits light emitted from a measurement light source 102 into the measurement light (sample light) and the reference light by use of a coupler (light splitter) 104. Then, the OCT optical system 100 introduces the measurement light to the anterior segment by a measurement optical system 106 and also introduces the reference light to a reference optical system 110. After that, interference light, which is a synthesis result of the measurement light reflected on the anterior segment and the reference light, is received by the detector (light receiving element) 120.

The light emitted from the light source 102 is split into a measurement beam and a reference beam by the coupler 104. The measurement beam passes an optical fiber, and then is emitted out to the air. The light beam is then collected in the anterior segment via the optical scanner 108 and other optical components of the measurement optical system 106. Then, the light reflected on the anterior segment comes back to the optical fiber through a similar optical path.

The optical scanner 108 scans the measurement light in the X-Y direction (lateral direction) on the eye E. The optical scanner 108 is, for example, two galvano mirrors, and a reflection angle of the scanner 108 is arbitrarily adjusted by a driving mechanism 109.

Thus, the light beam emitted from the light source 102 is changed its reflection (traveling) direction and scanned in an arbitrary direction on the eye E. Thereby, an imaging position on the anterior segment is changed. The optical scanner 108 may be the one having a configuration that reflects light. For example, as well as a reflection mirror (a galvano mirror, a polygon mirror, and a resonant scanner), an acousto-optic modulator (AOM) and others that change a traveling (deflection) direction of light are adopted.

The reference optical system 110 creates the reference light which is synthesized with reflection light obtained by reflection of the measurement light on the eye E. The reference optical system 110 may be a Michelson optical system or a Mach-Zehnder optical system. For example, the reference optical system 110 is formed with a reflective optical system (for example, a reference mirror) to bring back the light to the coupler 104 by reflecting the light from the coupler 104 by the reflective optical system and introduce the light to the detector 120. As an alternative example, the reference optical system 110 is formed with a transmission optical system (for example, an optical fiber) to transmit and introduce the light to the detector 120 without bringing the light back to the coupler 104.

The reference optical system 110 has a configuration that changes a difference in optical path lengths of the measurement light and the reference light by moving an optical component in a reference optical path. For example, the reference mirror is moved in an optical axial direction. The configuration for changing the difference in the optical path lengths may be arranged in a measurement optical path of the measurement optical system 106.

The detector 120 detects the interference state of the measurement light and the reference light. In a case of a Fourier domain OCT, a spectral intensity of the interference light is detected by the detector 120, and a depth profile (A scan signal) in a predetermined range is obtained by Fourier transform of the spectral intensity data. The controller 80 controls the optical scanner 108 to scan the measurement light on the anterior segment in a predetermined lateral direction, and thereby a tomographic image can be obtained. In other words, a tomographic image of the anterior segment of the examinee's eye is imaged. For example, by scanning in the X direction or the Y direction, a tomographic image (the tomographic image of the anterior segment) on an X-Z surface or a Y-Z surface of the anterior segment of the examinee's eye can be obtained (in the present embodiment, a method for thus obtaining the tomographic image by one-dimensionally scanning the measurement light relative to the anterior segment is referred to as a B scan). The obtained anterior segment tomographic image is stored in a memory 85 connected to the controller 80. Further, by two-dimensionally scanning the measurement light in the X-Y direction, it is possible to obtain a three-dimensional image of the anterior segment of the examinee's eye.

Examples for the Fourier domain OCT, a Spectral-domain OCT (SD-OCT) and a Swept-source OCT (SS-OCT) are given. Further, a Time-domain OCT (TD-OCT) may also be adopted.

For the SD-OCT, a low coherent light source (broadband light source) is used as the light source 102, and the detector 120 is provided with a spectroscopic optical system (spectrometer) dispersing the interference light into each frequency component (each wavelength component). The spectrometer is, for example, made up of a diffraction grating and a line sensor.

For the SS-OCT, as the light source 102, a wavelength scanning light source (wavelength variable light source) changing an outgoing wavelength at temporally high-speed is used, and as the detector 120, for example, a single light receiving element is provided. The light source 102 is, for example, constituted with a light source, a fiber ring resonator, and a wavelength selectable filter. As the wavelength selectable filter, for example, a combination of a diffraction grating and a polygon mirror and a Fabry-Perot Etalon filter may be adopted.

The corneal shape measuring device 300 is roughly divided into a corneal projection optical system 50, an alignment projection optical system 40, and a front image of an anterior segment imaging optical system 30.

The corneal projection optical system 50 has ring-shaped light sources 51 arranged around a measurement optical axis L1 and is used for measuring a corneal shape (a curvature, an astigmatic axial angle, and others) by projecting a ring target on a cornea of the examinee's eye. An LED emitting infrared light or visible light is used as the light sources 51, for example. Incidentally, in the projection optical system 50, at least three point light sources may be arranged on the same circumference centering on the optical axis L1, and therefore the light source may be an intermittent ring light source. Furthermore, the projection optical system 50 may be a Placido target projecting optical system projecting a plurality of ring targets.

The alignment projection optical system 40 arranged inside the light sources 51 has projection light sources 41 (for example, λ=970 nm) emitting infrared light and is used for projecting an alignment target on a cornea Ec of the examinee's eye. The alignment target projected on the cornea Ec is used for alignment with respect to the examinee's eye (for example, automatic alignment, alignment detection, manual alignment, and others). In the present embodiment, the projection optical system 50 is an optical system for projecting the ring target on the cornea Ec of the examinee's eye, and the ring target also serves as a mire ring. The light sources 41 of the projection optical system 40 serve as illumination for the anterior segment, illuminating the anterior segment with the infrared light in a helical direction. In the projection optical system 40, an optical system projecting parallel light on the cornea Ec may further be provided so that front and back alignment is conducted by a combination of the parallel light and limited light of the projection optical system 40.

The front image of the anterior segment imaging optical system 30 is used for imaging (obtaining) a front image of the anterior segment. The imaging optical system 30 includes a dichroic mirror 33, an objective lens 47, a dichroic mirror 62, a filter 34, an imaging lens 37, and a two-dimensional imaging device 35. The imaging optical system 30 is used for imaging the front image of the anterior segment of the examinee's eye. The two-dimensional imaging device 35 is arranged in a position almost conjugate with the anterior segment of the examinee's eye.

The reflection light of the anterior segment reflected by the aforementioned projection optical systems 40 and 50 is formed as an image in the two-dimensional imaging device 35 via the dichroic mirror 33, the objective lens 47, the dichroic mirror 62, the filter 34, and the imaging lens 37.

The axial length measuring device 10 is formed with a light projecting optical system and a light receiving optical system, and the light projecting optical system is provided with a measuring light source 1 emitting low coherent light. The light emitted from the light source 1 is split into the measurement light and the reference light, and at least the measurement light is irradiated on the examinee's eye. Then, the reflection light from the examinee's eye and the reference light are synthesized and brought into the light receiving element. Based on a light receiving signal output from the light receiving element, the axial length is calculated according to timing when the interference light is detected by the light receiving element. In the present embodiment, the measuring light source of the axial length optical system 10 serves as a fixation lamp.

Further, for example, a large part of reflection light of a fundus obtained by the reflection of light emitted from the light source 1 is transmitted through the dichroic mirror 33 and received by the light receiving element of the axial length measuring optical system 10. A part of the reflection light of the fundus is reflected on the dichroic mirror 33 and formed as an image in the front image of the anterior segment imaging optical system 30.

Next, a control system is explained. The controller 80 controls the whole apparatus and calculates measurement results. The controller 80 is connected to each component of the OCT device 5, each component of the axial length measuring device 10, each component of the corneal shape measuring device 300, a monitor 70, an operation part 84, a memory 85, and others.

In the present embodiment, an axial length measuring mode for measuring an axial length and an anterior segment measuring mode for measuring an anterior segment (for example, a corneal shape or the like) from a cross-sectional image of the anterior segment are prepared. Either mode is selected automatically or manually.

In the operation part 84, a general interface such as a mouse may be used as an operation input part. Alternatively, a touch screen may be used. Further, in the operation part 84, for example, a mode selector switch 84a is provided for switching the axial length measuring mode for measuring the axial length and the anterior segment measuring mode for measuring the anterior segment (for example, the corneal shape or the like) from the cross-sectional image of the anterior segment.

In the memory 85, as well as various control programs, a software program instructing the controller 80 to calculate the axial length or the corneal shape, a software program instructing the controller 80 to calculate the IOL power, and others are stored.

<Anterior Segment Measuring Mode>

An operation of the above-configured apparatus is now explained. The following explanation is made for the anterior segment measuring mode. An operator uses a not-shown operating member such as a joy stick to move the apparatus in lateral and longitudinal directions and in a back and forth direction while checking an alignment state of the examinee's eye displayed on the monitor 70 so that the apparatus is arranged in a predetermined position with respect to the examinee's eye E. At this time, the operator makes the examinee's eye fixate a fixation target.

Figure 2:
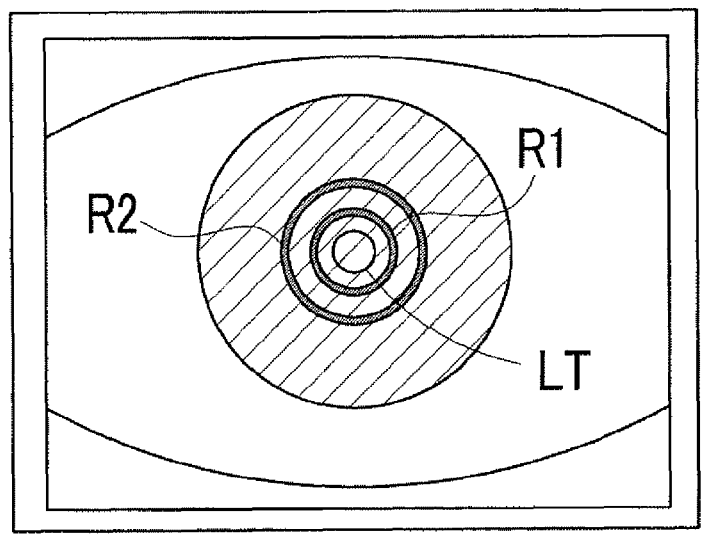
FIG. 2 is a view showing an anterior segment observation screen displayed with an image of an anterior segment.

FIG. 2 is a view showing an anterior segment observation screen displayed with an image of the anterior segment imaged by the imaging device 35. When alignment, the light sources 41 and 51 are illuminated. Further, the light source 102 of the OCT device 5 is illuminated. The operator conducts the alignment in the lateral and longitudinal directions so that an electronically displayed reticle LT and a ring target R1 from the light source 41 are concentrically arranged as shown in FIG. 2. Further, the operator conducts the alignment in the back and forth direction so that the ring target R1 comes into focus. A ring target R2 from the light source 51 is displayed outside the ring target R1.

After the alignment to the anterior segment is completed, the controller 80 controls the OCT optical system 100 to obtain a tomographic image based on a preset scanning pattern, and the obtained tomographic image is displayed as a moving image on the monitor 70.

First, a corneal shape measurement is conducted. In the present embodiment, a corneal curvature radius on a front surface of a cornea is calculated using the corneal shape measuring device 300, and a corneal curvature radius on a back surface of the cornea is calculated using the OCT device 5. After the alignment is conducted as mentioned above and a predetermined trigger signal is given off, the controller 80 photographs an image of the anterior segment. Then, the controller 80 conducts each calculation for the corneal shape (for example, the corneal curvature radius on the corneal front surface in a strong principal meridian direction and in a weak principal meridian direction, an astigmatic axial angle of the cornea, and others) of the examinee's eye based on the ring targets R1 and R2 on the anterior segment image which is stored in the memory 85. Then, the measurement result is stored in the memory 85.

Next, photographing of a cross-sectional image of the anterior segment is conducted. The controller 80 obtains a tomographic image of the anterior segment and stores the obtained image data (for example, as a still image) in the memory 85. The anterior segment tomographic image obtained by the OCT optical system 100 can be photographed in a range including a tomographic image of a back surface of the lens. Therefore, the controller 80 is able to process (analyze) the obtained anterior segment tomographic image and measure the anterior segment (in the present embodiment, the corneal curvature radius of the corneal back surface, an anterior chamber depth, a corneal thickness, a front surface curvature of the lens, a back surface curvature of the lens, a lens thickness).

In the present embodiment, an alignment reference point is defined as a position where a corneal vertex position and an optical axis (L1) of the apparatus coincide each other, and then the alignment is conducted. In other words, the alignment is conducted such that a scanning point passes the corneal vertex point when the anterior segment tomographic image is obtained.

<Axial Length Measurement>

Next, the axial length measuring mode is explained. The operator uses a not-shown operating member such as a joy stick to move the apparatus in the lateral and longitudinal directions and in the back and forth direction while checking the alignment state of the examinee's eye displayed on the monitor 70 so that the apparatus is arranged in a predetermined position with respect to the examinee's eye E.

After the alignment is completed, a trigger signal for starting a measurement is automatically or manually given off, and the measuring light source 1 is illuminated by the controller 80. After that, the measurement light is irradiated on the examinee's eye by the axial length measuring device 10, and reflection light from the examinee's eye by the measurement light is entered in the light receiving element of the axial length measuring device 10. Then, based on a light receiving signal output from the light receiving element, the axial length is calculated according to timing when interference light is detected by the light receiving element.

<IOL Power Calculation>

After the measurement by the axial length measuring mode and the anterior segment measuring mode is finalized as mentioned above, the controller 80 calculates the IOL power based on the obtained measurement data.

As a calculation method for the IOL power, a known SRK/T formula, Binkhors formula, and others are partially applied. For example, when applying the SRK/T formula, parameters of the corneal curvature radius, the axial length, a lens constant (when the SRK/T formula is used, the constant is called A-constant) are used for the IOL power calculation.

The controller 80 obtains an offset distance from a front surface of the lens to a point of contact of a Zinn's zonule with the lens based on the cross-sectional image of the anterior segment which is obtained by the OCT device 5. The controller 80 then calculates a prospective postoperative anterior chamber depth by adding the offset distance to an anterior chamber depth of the eye, and the IOL power calculation is conducted using the prospective postoperative anterior chamber depth.

Figure 3:
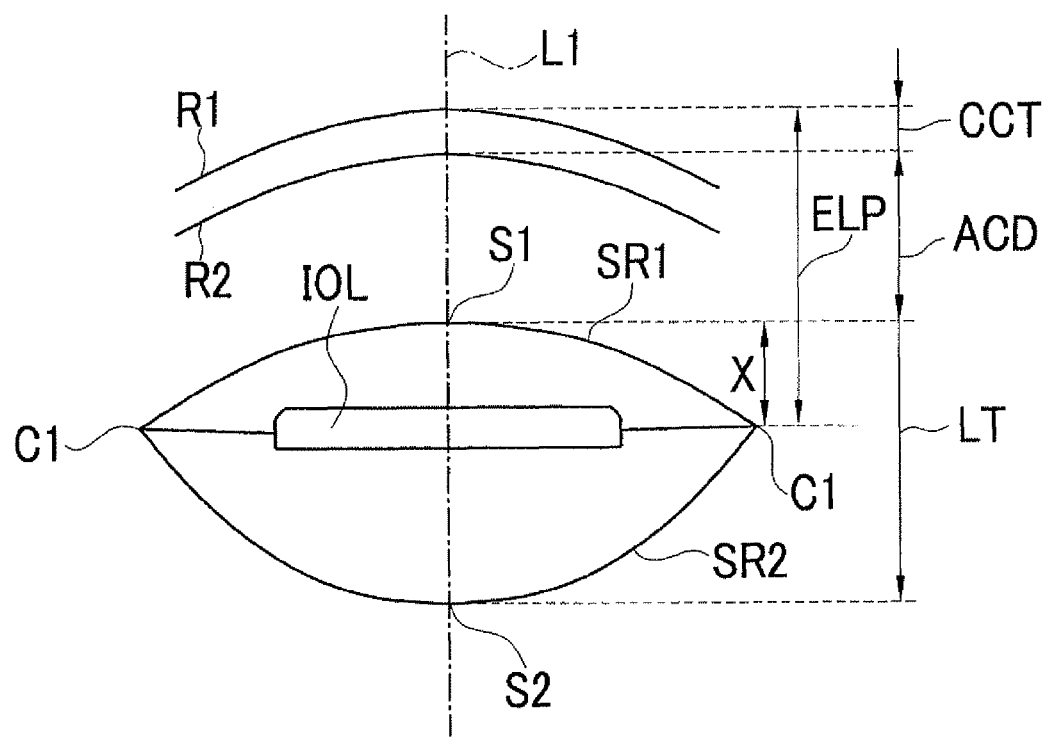
FIG. 3 is an explanatory view explaining a calculation of an IOL power.

A detailed explanation is given with reference to FIG. 3. First, a corneal height from a front surface of the cornea to the front surface of the lens is calculated from a corneal thickness CCT and an anterior chamber depth ACD. To the corneal height, a correction amount α (function of the A-constant), which is different in offset amounts (offset distances) X and types of IOL, is added, and thereby a prospective postoperative anterior chamber depth ELP is calculated. Then, the IOL power is calculated from the prospective postoperative anterior chamber depth ELP, an axial length measurement result AL, and the corneal curvature radius.

The offset amount X represents a distance from a front surface vertex S1 of the lens after the IOL is injected to a support part of the IOL (approximately a position of an optical part of the IOL). Incidentally, the offset amount X is not considered a moving amount (the correction amount α mentioned above) of the IOL moved toward a lens posterior capsule by the pressure from a lens capsule, and the moving amount is removed (a detailed explanation is given later). A position of the IOL support part is similar to a point of contact C1 of the Zinn's zonule with the lens (for example, an intersection of the lens front surface and the lens back surface).

The corneal thickness CCT and the anterior chamber depth ACD hardly yield errors since they are the measurement results. On the other hand, the offset amount X tends to yield an error in a case that the amount is determined mainly with the A-constant as a parameter based on numerous clinical data.

As follows, a method for more precisely calculating the offset amount X is explained. In the present embodiment, the controller 80 obtains at least either one of: lens front surface information (lens front surface curvature radius) R3 of a lens front surface SR1; lens back surface information (lens back surface curvature radius) R4 of a lens back surface SR2; or lens thickness information (a lens thickness) LT as figure information of the lens of the examinee's eye. Then, the offset distance is calculated based on the obtained figure information. Namely, for precisely calculating the offset amount X, a profile of the lens according to the examinee's eye needs to be obtained.

As a method for calculating the lens front surface curvature radius R3, for example, the controller 80 detects three points along the lens front surface based on a concentration value (luminance value) corresponding to the lens front surface on the cross-sectional image of the anterior segment which is obtained by the OCT device 5. Then, the detected three points circularly approximate the lens front surface to obtain a curvature center O4. The lens front surface curvature radius R3 is calculated from the distance from the curvature center O4 to the lens front surface. As a method for calculating the lens back surface curvature radius R4, the controller 80 detects three points along the lens back surface based on the concentration value (luminance value) corresponding to the lens back surface on the cross-sectional image of the anterior segment which is obtained by the OCT device 5. Then, the detected three points circularly approximate the lens back surface to obtain a curvature center O3. The lens back surface curvature radius R4 is thus calculated from the distance from the curvature center O3 to the lens back surface.

First, the lens front surface curvature radius R3, the lens back surface curvature radius R4, and the lens thickness LT are used to calculate a position of the point of contact of the Zinn's zonule with the lens. The position of the contact point of the Zinn's zonule and the lens is a portion where the IOL support part is located when the IOL is injected. Therefore, a position of the postoperative IOL support part can be calculated by calculating the position of the contact point of the Zinn's zonule and the lens. Further, the position of the postoperative IOL support part is similarly referred to as the IOL's position, and thereby the IOL's position can be calculated by calculating the position of the postoperative IOL support part. Thus, the offset amount X is calculated.

Figure 4:
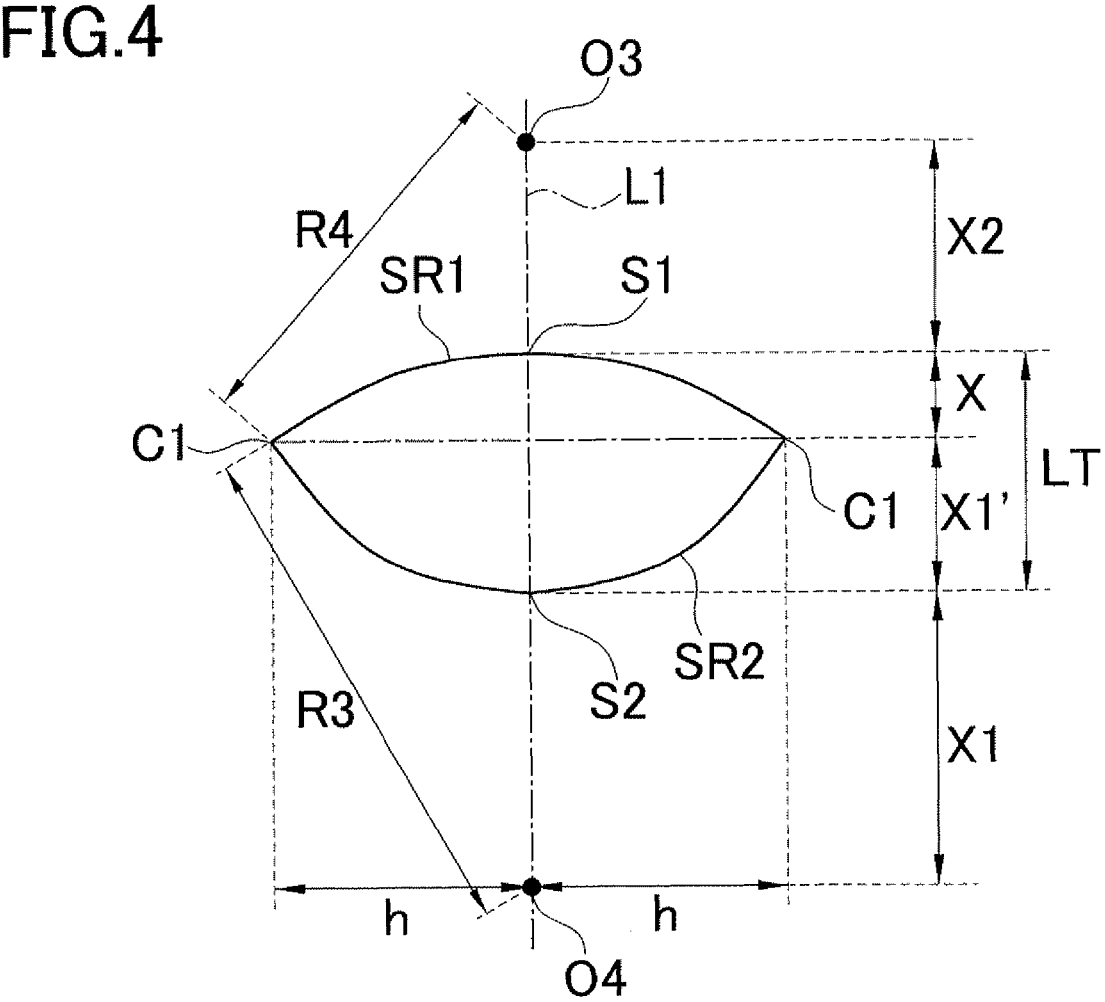
FIG. 4 is an explanatory view explaining a calculation method of an offset amount.

Specifically, the offset amount X is obtained as follows. FIG. 4 is an explanatory view explaining a method for calculating the offset amount X. A reference sign h indicates a distance from the optical axis L1 to the contact point of the Zinn's zonule of the lens and the lens. X1 indicates a distance from the lens front surface curvature center O4 on the optical axis L1 to the lens back surface. X1' indicates a distance from the contact point of the Zinn's zonule and the lens to a lens back surface vertex S2. X2 indicates a distance from the lens back surface curvature center O3 on the optical axis L1 to a lens front surface vertex S1. X is the offset amount, indicating a distance from the contact point of the Zinn's zonule and the lens to the lens front surface.

The following equation is given according to the Pythagorean theorem.

$$h = \sqrt{R_3^2 - (X1 + X1')^2} = \sqrt{R_3^2 - (R_3 - X)^2}$$

$$h = \sqrt{R_4^2 - (X2 + X)^2} = \sqrt{R_4^2 - (R_4 - LT + X)^2} \quad \text{Equation 1}$$

Since "h" is the same in the above equations, these equations are expanded to hold the following equation.

$$X = \frac{2R_4 LT - LT^2}{2(R_3 + R_4 - LT)} \quad \text{Equation 2}$$

To be specific, since the offset amount X is calculated by using the measurement value which is actually measured, the offset amount X with less error can be calculated.

Then, from the calculated offset amount X, the prospective postoperative anterior chamber depth ELP is calculated. The anterior chamber depth ELP is calculated based on the offset amount X, the anterior chamber depth ACD, the corneal thickness CCT, and the correction amount α.

Figure 5:
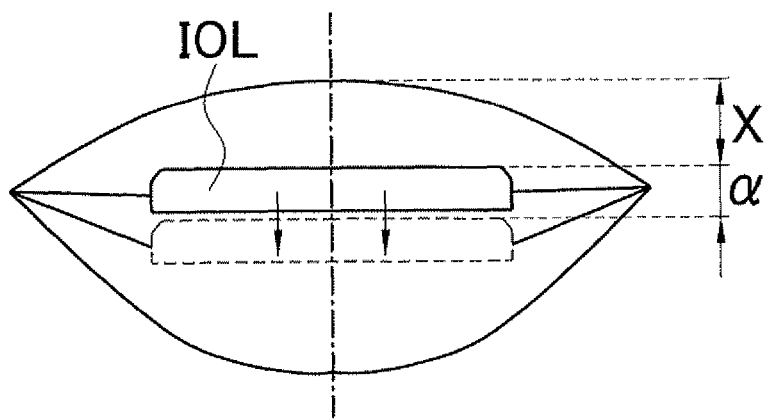
FIG. 5 is an explanatory view explaining a correction amount.

The correction amount α is, as shown in FIG. 5, a parameter for correcting the moving amount of the IOL when the IOL is pushed toward a posterior capsule of the lens by the pressure of the lens capsule after injection of the IOL. When the IOL is pushed toward the posterior capsule, the IOL is slightly moved toward the posterior capsule. Specifically, the prospective postoperative anterior chamber depth ELP can be more precisely calculated by correcting the moving amount of the IOL toward the posterior capsule and calculating the anterior chamber depth ELP. Since the moving amount differs depending on a structure, material, and others of the IOL, the correction amount α is calculated by a known function using the A-constant which is determined depending on a type of the IOL. In other words, the prospective postoperative anterior chamber depth is corrected by the A-constant which is specific to each IOL. The A-constant is determined and stored in the memory 85 in advance.

The prospective postoperative anterior chamber depth ELP is obtained as follows.

$$ELP = CCT + ACD + X + \alpha \quad \text{Equation 3}$$

As above, the offset amount X is calculated by further adding measured values such as the figure information of the lens, and thereby the highly accurate prospective postoperative anterior chamber depth ELP is calculated. Then, the IOL power can be precisely calculated by using the anterior chamber depth ELP and the axial length measurement result.

In the present invention, the corneal curvature of the corneal front and back surfaces and the corneal thickness are each calculated, and the IOL power is calculated based on the measured values. Therefore, the IOL power can be precisely calculated even for an examinee's eye which has changes or abnormalities in a corneal shape. For example, the present invention is especially valuable to an examinee's eye having a changed corneal shape such as an eye after having the LASIK surgery since the IOL power calculation is conducted in a manner that changes of the corneal shape (corneal curvature and corneal thickness) are considered.

The present invention is applicable to a case that a three-dimensional figure image is obtained by obtaining a tomographic image of an anterior segment at a plurality of scanning points by an optical coherence tomography device for photographing a tomographic image (cross-sectional image) of an anterior segment. The OCT device 5 is an anterior segment imaging device for obtaining a three-dimensional cross-sectional image of the anterior segment (three-dimensional anterior segment data). The controller 80 is to three-dimensionally obtain an offset distance from a lens front surface to a point of contact of a Zinn's zonule with the lens based on the three-dimensional cross-sectional image which is obtained by this anterior segment imaging device. In this case, an average of a corneal front surface curvature and a corneal back surface curvature in each meridian direction in the three-dimensional anterior segment data is calculated, and then ELP is calculated based on this average value. By obtaining a measured value from the three-dimensional figure image, the obtained measurement value becomes accurate.

As an anterior segment imaging device imaging a cross-sectional image of the anterior segment, the present embodiment is explained with exemplifying an optical coherence tomography device for photographing a tomographic image (cross-sectional image) of an anterior segment, but the device is not limited to this. The device may be the one having a configuration that includes: a light projecting optical system projecting light emitted from a light source to the anterior segment of an examinee's eye and forming a light sectional surface on the anterior segment; and a light receiving optical system having a detector for receiving light including scattered light of the anterior segment obtained by scattering of the light sectional surface on the anterior segment so that a cross-sectional image of the anterior segment is formed based on a detection signal from the detector. To be specific, it is applicable to an apparatus projecting slit light on the anterior segment of the eye and obtaining the cross-sectional image of the anterior segment by a Scheimpflug camera.

The present invention is also applicable to an apparatus for obtaining a three-dimensional figure image of the anterior segment by rotating a Scheimpflug camera. In this case, the three-dimensional figure image of the anterior segment can be precisely obtained by conducting a displacement correction at each predetermined rotation angle, and thereby a measurement value obtained by the three-dimensional figure image becomes more accurate. In this case, a displacement in a vertical direction with respect to an imaging surface (slit sectional surface) is detected, and the displacement correction is conducted based on the detection result.

In the above configuration, the cross-sectional image of the anterior segment is optically obtained, but the configuration is not limited to this. The device may be an anterior segment imaging device obtaining the anterior segment cross-sectional image by detecting reflection from the anterior segment of the examinee's eye. For example, the configuration may be the one that obtains the anterior segment cross-sectional image by detecting reflection information from the anterior segment using an ultrasonic probe for B scan.

The present embodiment adopts an IOL calculation formula such as a known SRK/T formula and Binkhors formula as a method for calculating the IOL power, but the method is not limited to this. For example, the IOL power can be calculated by an optical ray tracing method which geometrically traces reflection and refraction of light using rays of light and simulates a behavior of the light. In this case, the IOL power is calculated by the optical ray tracing method using the prospective postoperative anterior chamber depth ELP, the corneal thickness CCT, an axial length measurement result AL, the corneal curvature radius of the corneal front surface, and the corneal curvature radius of the corneal back surface. The optical ray tracing method is to calculate the IOL power by simulating the reflection and the refraction of the light, and therefore the IOL power can be more precisely calculated than the theoretical IOL formula.

In the present embodiment, the corneal curvature radius of the corneal front surface is calculated by the corneal shape measuring device 300, and the corneal curvature radius of the corneal back surface is calculated by the OCT device 5, but the configuration is not limited to this. The corneal curvature radius of the corneal front and back surfaces may be calculated by the OCT device 5. Alternatively, a similar measured value may be treated as the corneal curvature radius of the corneal front and back surfaces. Namely, the corneal curvature radius of the corneal front surface calculated by the corneal shape measuring device 300 is used as the corneal curvature radius of the corneal front and back surfaces.

In the present embodiment, a corneal topography may be used as the corneal shape measuring device 300. In this case, the curvature radius of the corneal front surface is calculated from the whole shape of the cornea when the curvature radius is calculated, and thereby the curvature radius of the corneal front surface is precisely calculated. Therefore, precision of the IOL power calculation is improved when calculating the IOL power.

In the present embodiment, the controller 80 processes the cross-sectional image of the anterior segment obtained by the OCT device 5 to obtain the figure information of the lens of the examinee's eye and calculates the offset distance X based on the obtained figure information, but the configuration is not limited to this.

In a case that the OCT device 5 is an anterior segment imaging device (for example, an ultrasonic B probe or an anterior segment OCT) capable of imaging the cross-sectional image of the anterior segment including a ciliary body, the controller 80 obtains the offset distance X based on positional information of the ciliary body on the anterior segment cross-sectional image obtained by the OCT device 5. For instance, the ciliary body (an end portion of the ciliary body) is detected from the obtained tomographic image of the anterior segment (anterior segment cross-sectional image), and a position of the Zinn's zonule is estimated from the detected position of the ciliary body. Then, a position of the contact point of the Zinn's zonule and the lens may be detected from thus estimated position of the Zinn's zonule.

Further, in a case that the OCT device 5 is an anterior segment imaging device (for example, an ultrasonic B probe or an anterior segment OCT) capable of imaging the cross-sectional view of the anterior segment including the point of contact of the Zinn's zonule with the lens, the controller 80 obtains the offset distance X by processing the contact point on the anterior segment cross-sectional image obtained by the OCT device 5. For instance, when the Zinn's zonule is photographed on the tomographic image (cross-sectional image) of the anterior segment, the contact point of the Zinn's zonule and the lens may be detected from the obtained anterior segment tomographic image.

The present invention is not limited to the apparatus disclosed above in the present embodiment. For example, an IOL power calculation software (program) having a function of the above embodiment may be supplied to a system or an apparatus via a network or various storage media. Then, a computer (for example, a CPU or the like) of the system or the apparatus may read out and execute the program.

REFERENCE SIGNS LIST

5 Optical coherence tomography device
10 Axial length measuring device
30 Front image of an anterior segment imaging optical system
40 Alignment projection optical system
50 Corneal projection optical system
70 Monitor
80 Controller
84 Operation part
85 Memory

The invention claimed is:

1. An intraocular lens power determination method including the steps of:
   obtaining a cross-sectional image of an anterior segment of an examinee's eye by detecting reflection from the anterior segment using an anterior segment imaging device;
   obtaining an offset distance from a front surface of a lens to a point of contact of a Zinn's zonule with the lens based on the anterior segment cross-sectional image; and
   calculating a prospective postoperative anterior chamber depth by adding the offset distance to an anterior chamber depth of an eye,
   wherein an intraocular lens power is calculated by using the prospective postoperative anterior chamber depth, and the prospective postoperative anterior chamber depth is corrected by an A-constant specific to each intraocular lens.

2. The intraocular lens power determination method according to claim 1, the method further including the steps of:
   obtaining figure information of the lens of the examinee's eye by processing the anterior segment cross-sectional image; and
   calculating the offset distance based on the obtained figure information.

3. The intraocular lens power determination method according to claim 2, the method further including the steps of:
   obtaining figure information including at least one of lens front surface information, lens back surface information, and lens thickness information as figure information of the lens of the examinee's eye; and
   calculating the offset distance based on the obtained figure information.

4. The intraocular lens power determination method according to claim 1, the method further including the steps of:

obtaining the anterior segment cross-sectional image using the anterior segment imaging device capable of imaging a cross-sectional image of the anterior segment including the point of contact of the Zinn's zonule with the lens; and obtaining the offset distance by processing the contact point on the anterior segment cross-sectional image.

5. An intraocular lens power determination apparatus comprising:

an anterior segment imaging device arranged to obtain a cross-sectional image of an anterior segment by detecting reflection from the anterior segment of an examinee's eye; and a power calculation unit arranged to obtain an offset distance from a front surface of a lens to a point of contact of a Zinn's zonule with the lens based on the anterior segment cross-sectional image obtained by the anterior segment imaging device, calculate a prospective postoperative anterior chamber depth by adding the offset distance to an anterior chamber depth of an eye, and conduct an intraocular lens power calculation using the prospective postoperative anterior chamber depth.

6. The intraocular lens power determination apparatus according to claim 5, wherein the power calculation unit obtains figure information of the lens of the examinee's eye by processing the anterior segment cross-sectional image obtained by the anterior segment imaging device and calculates the offset distance based on the obtained figure information.

7. The intraocular lens power determination apparatus according to claim 6, wherein the power calculation unit obtains figure information including at least one of lens front surface information, lens back surface information, and lens thickness information as the figure information of the lens of the examinee's eye and calculates the offset distance based on the obtained figure information.

8. The intraocular lens power determination apparatus according to claim 5, wherein the anterior segment imaging device is configured to image a cross-sectional image of the anterior segment including the point of contact of the Zinn's zonule with the lens, and the power calculation unit obtains the offset distance by processing the point of contact on the anterior segment cross-sectional image obtained by the anterior segment imaging device.

9. The intraocular lens power determination apparatus according to claim 5, wherein the anterior segment imaging device is configured to image the cross-sectional image of the anterior segment including a ciliary body, and the power calculation unit obtains the offset distance based on positional information of the ciliary body on the anterior segment cross-sectional image obained by the anterior segment imaging device.

10. The intraocular lens power determination apparatus according to claim 5, wherein the anterior segment imaging device is arranged to obtain a three-dimensional cross-sectional image of the anterior segment, and the power calculation unit is arranged to three-dimensionally obtain the offset distance from the front surface of the lens to the point of contact of the Zinn's zonule with the lens based on the three-dimensional cross-sectional image obtained by the anterior segment imaging device.

11. The intraocular lens power determination apparatus according to claim 5, wherein the power calculation unit corrects the prospective postoperative anterior chamber depth by an A-constant specific to each intraocular lens.

12. The intraocular lens power determination apparatus according to claim 5, wherein the anterior segment imaging device is any one of an optical coherence tomography device, a Scheimpflug camera, or an ultrasonic probe.

13. An intraocular lens power determination program recorded on a non-transitory computer readable medium product and instructing a computer to execute:

a first step of obtaining an offset distance from a front surface of a lens to a point of contact of a Zinn's zonule with the lens based on a cross-sectional image of an anterior segment obtained by an anterior segment imaging device;

a second step of calculating a prospective postoperative anterior chamber depth by adding the offset distance in the first step to an anterior chamber depth of an eye; and a third step of conducting an intraocular lens power calculation using the prospective postoperative anterior chamber depth calculated in the second step.

14. The intraocular lens power determination program according to claim 13, instructing the computer to further execute:

a fourth step of obtaining figure information of the lens of the examinee's eye by processing the anterior segment cross-sectional image; and a fifth step of calculating the offset distance based on the obtained figure information.

15. The intraocular lens power determination program according to claim 14, instructing the computer to further execute:

a sixth step of obtaining figure information including at least one of lens front surface information, lens back surface information, and lens thickness information as figure information of the lens of the examinee's eye; and a seventh step of calculating the offset distance based on the obtained figure information.

16. The intraocular lens power determination program according to claim 13, instructing the computer to further execute:

a fourth step of obtaining the anterior segment cross-sectional image using the anterior segment imaging device capable of imaging a cross-sectional image of the anterior segment including the point of contact of the Zinn's zonule with the lens; and a fifth step of obtaining the offset distance by processing the contact point on the anterior segment cross-sectional image.

17. The intraocular lens power determination program according to claim 13, instructing the computer to further execute:

a fourth step of obtaining the anterior segment cross-sectional image using the anterior segment imaging device capable of imaging the anterior segment cross-sectional image including a ciliary body; and a fifth step of obtaining the offset distance based on positional information of the ciliary body on the anterior segment cross-sectional image.

18. The intraocular lens power determination program according to claim 13, instructing the computer to further execute:

a fourth step of obtaining a three-dimensional cross-sectional image of the anterior segment using the anterior segment imaging device capable of obtaining the three-dimensional cross-sectional image of the anterior segment; and a fifth step of obtaining the offset distance from the front surface of the lens to the point of contact of the Zinn's zonule with the lens based on the three-dimensional cross-sectional image.

19. The intraocular lens power determination program according to claim 13, wherein the prospective postoperative anterior chamber depth is corrected by an A-constant specific to each intraocular lens.

20. The intraocular lens power determination program according to claim 13, wherein the anterior segment imaging device is any one of an optical coherence tomography device, a Scheimpflug camera, or an ultrasonic probe.

* * * * *